United States Patent
Arnoud et al.

(10) Patent No.: US 7,144,965 B2
(45) Date of Patent: Dec. 5, 2006

(54) HALOGENATED STYRENE COMPOUNDS AND VERY LOW-LOSS POLYMERS MADE THEREFROM

(75) Inventors: Olivier Arnoud, Vincennes (FR); Marc Moroni, Paris (FR); Stephane Roux, Charenton de Pont (FR)

(73) Assignee: Corning, Incorporated, Corning, NY (US)

( * ) Notice: Subject to any disclaimer, the term of this patent is extended or adjusted under 35 U.S.C. 154(b) by 211 days.

(21) Appl. No.: 11/018,726

(22) Filed: Dec. 20, 2004

(65) Prior Publication Data

US 2005/0113520 A1 May 26, 2005

Related U.S. Application Data

(62) Division of application No. 10/667,530, filed on Sep. 22, 2003, now Pat. No. 6,891,071.

(30) Foreign Application Priority Data

Oct. 18, 2002 (EP) .................................. 02292461

(51) Int. Cl.
*C08F 28/06* (2006.01)
(52) U.S. Cl. ...................... 526/257; 526/248; 526/251; 526/252; 526/262; 526/347
(58) Field of Classification Search ................ 526/248, 526/251, 252, 257, 262, 347
See application file for complete search history.

(56) References Cited

U.S. PATENT DOCUMENTS

| | | | |
|---|---|---|---|
| 3,637,866 A | 1/1972 | De Pasquale et al. | .. 260/612 R |
| 3,661,967 A | 5/1972 | Anderson et al. | ........ 260/465 F |
| 5,391,587 A | 2/1995 | Wu | .............................. 522/40 |
| 6,369,279 B1 | 4/2002 | Nakashima et al. | ........ 568/630 |

FOREIGN PATENT DOCUMENTS

| | | |
|---|---|---|
| JP | 06016615 | 1/1994 |
| JP | 06157501 | 6/1994 |
| JP | 08333322 | 12/1996 |
| JP | 10001457 | 1/1998 |
| JP | 10316642 | 12/1998 |
| JP | 2000327622 | 11/2000 |
| JP | 2000327629 | 11/2000 |
| JP | 2000327652 | 11/2000 |
| JP | 61-114211 | 5/2001 |

OTHER PUBLICATIONS

"Synthesis and characterization of 4-[per/polyfluoro)phenyloxy]-4'-vinylbiphenyls and their polymers" I.I. Selvaraj, et al, Dept. of Chemistry Polymer 40 1999 pp. 6575-6582.

*Primary Examiner*—Helen L. Pezzuto
(74) *Attorney, Agent, or Firm*—Walter M. Douglas (57) ABSTRACT

The invention is directed to polymerizable vinyl compounds having halogenated aromatic groups and to a method of synthesizing such compounds. In particular, the invention is directed to polymerizable aromatic vinyl compounds wherein, except for the vinylic hydrogen atoms, aromatic C—H bonds are replaced by C—X bonds, where X is a halogen or other selected substituent having a de minimus number, if any, of C—H bonds; for example, without limitation, highly fluorinated fluoroalkanes. In addition, the compounds of the invention have a de minimus number, if any, of N—H and O—H bonds.

12 Claims, 3 Drawing Sheets

HALOGENATED STYRENE COMPOUNDS AND VERY LOW-LOSS POLYMERS MADE THEREFROM

CLAIM OF PRIORITY

This application claims the priority benefit of European Application Number 02292461.7 filed Oct. 18, 2002 and U.S. application Ser. No. 10/667,530 filed Sep. 22, 2003, now U.S. Pat. No. 6,891,071.

FIELD OF THE INVENTION

The invention is directed to novel aromatic vinyl compounds, methods of preparing such compounds, and their use as polymeric materials. In particular, the invention is directed to low-loss, halogenated styrene compounds and their derivatives that can be used in optical communications devices.

BACKGROUND OF THE INVENTION

In optical communication systems, messages are transmitted by electromagnetic carrier waves at optical frequencies that are generated by sources such as lasers and light-emitting diodes. One preferred device for routing or guiding waves of optical frequencies from one point to another is an optical waveguide. The operation of an optical waveguide is based on the fact that when a light-transmissive medium is surrounded or otherwise bounded by an outer medium having a lower refractive index, light introduced along the axis of the inner medium substantially parallel to the boundary with the outer medium is highly reflected at the boundary, trapping the light in the light transmissive medium and thus producing a guiding effect between channels. A wide variety of optical devices can be made which incorporate such light guiding structures as the light transmissive elements. Examples, without limitation, include planar optical slab waveguides, channel optical waveguides, rib waveguides, optical couplers, optical splitters, optical switches, optical filters, arrayed waveguide gratings, waveguide Bragg gratings, variable attenuators and the like. For light of a particular frequency, optical waveguides may support a single optical mode or multiple modes, depending on the dimensions of the inner light guiding region and the difference in refractive index between the inner medium and the surrounding outer medium.

Organic polymeric materials can be used to construct optical waveguide and interconnect devices such as those given above. However, whereas single mode optical devices built from planar waveguides made from glass are relatively unaffected by temperature, devices made from organic polymers may show a significant variation of properties with temperature. This is due to the fact that organic polymeric materials have a relatively high thermo-optic coefficient (dn/dT). Consequently, a change in temperature causes the refractive index of an optical device made from a polymeric material to change appreciably. This ability to have a change in polymer refractive index due to a temperature change can be used to make active, thermally tunable or controllable devices incorporating light transmissive elements. One example of a thermally tunable device is a 1×2 switching element activated by the thermo-optic effect. In such a device light from an input waveguide may be switched between two output waveguides by the application of a thermal gradient induced by a resistive heater for which the heating/cooling processes occur over the span of one to several milliseconds.

A critical requirement for telecommunication devices is to achieve low insertion loss; which means that the materials used in waveguides and optical devices should have low levels of light absorption. While special, high purity glass has been used in many glass telecommunications applications, in recent years there has been considerable research into polymeric materials which can be used by the telecommunications industry instead of glass. Polymers have several advantages over glass materials. For example, they can be easily formulated to specifically match desired properties or can be reacted with other polymeric material to achieve the desired characteristics; and they can be worked at lower temperatures than glass. However, traditional carbon-hydrogen polymeric materials also have certain undesirable characteristics. In particular, when polymeric materials are used in telecommunications devices, the absorption in the near IR for organic materials is linked to the presence of E-H covalent bonds (E=N, O or C) that have stretching vibration bands at energies between 2800 and 3500 nm. Overtones and combinations bands involving these E-H bonds can increase significantly the absorption loss at 1550 nm. In addition, O—H and N—H bonds, which may be present in polyimides and polyacrylates for exemple, contribute very strongly to absorption at wavelengths near 1310 nm as well as at 1550 nm. Thus, the presence of O—H and N—H bonds is particularly detrimental to low losses. Thus, the presence of O—H and N—H bonds is particularly detrimental to low losses. Consequently, for telecommunications uses it would be desirable to produce polymerizable organic materials that have no or very few C—H, O—H and N—H bonds. Comparatively speaking, it is relatively easy to prepare polymerizable materials that do not contain O—H and N—H bonds. The removal of all C—H bonds from a molecular structure is a much more difficult task to accomplish.

Considerable research has been done concerning the replacement of C—H bonds by C—F bonds. However, very few organic materials are totally fluorinated, TEFLON being the best known example. In addition, even where monomeric C—H materials can be fully fluorinated, such perfluorinated monomers do not polymerize easily. Moreover, it is very difficult to process such the perfluoro polymers into telecommunications devices such as waveguides and planar devices.

While considerable efforts have been devoted to seeking polymerizable compounds having fluorinated alkyl attached to a polymerizable moiety, for example, an acrylate group, much less effort has been devoted to seeking novel polymerizable species in which the polymerizable group is directly attached to a fluorinated aromatic ring. Examples of compounds having fluorinated aromatic rings can be found in the following U.S. Pat. Nos. (title): U.S. Pat. No. 3,637,866 to Pasquale et al (Substituted Perfluoro Diphenyl Ethers); U.S. Pat. No. 3,661,967 to Anderson et al (Cyano Containing Polyfluoroaromatic Compounds); U.S. Pat. No. 4,420,225 to Bömer et al (Lens Of A Homo- Or Copolymer Of A Fluorine Containing Styrene Polymer); and U.S. Pat. No. 6,333,436 B1 (Styrene Derivatives). In particular, there are not many known compounds in which a fluorinated aromatic ring, and particularly highly fluorinated aromatic rings are directly attached to vinylic groups (—CH=CH$_2$).

Consequently, even though considerable research has been directed to the development of fluorine containing polymerizable materials, the need exists for addition materials in this area. In particular, there continues a need for fluorine containing polymerizable material that have low absorption losses in the 1550 nm and 1300 nm region in which telecommunications devices operate.

SUMMARY OF THE INVENTION

In one aspect, the invention is directed to halogenated aromatic compounds having polymerizable vinyl groups attached to the aromatic ring. The halogenated aromatic compounds of the invention are vinylbenzene (styrene) compounds in which the aromatic ring bearing the vinyl group is ring-substituted by fluorine, chlorine, and other fluorinated or chlorinated moieties, including mixtures of the foregoing moieties, and have the general formula $P_2C=CH-C_6X_{5-n}Z_n$, where P=H or D, $Z=-Y-C_6X_5$, $-Y-W-U-[(o-, m-, \text{ or } p-C_6X_4-CH=CH_2)]_m$ and mixtures thereof; Y and U, independently, are O, S, NH, or are absent; W is a linking group selected from the group consisting of aromatic, polycyclic aromatic (fused-ring), 5- or 6-member heterocyclic aromatic, and polycyclic-heterocyclic (fused ring) compounds containing carbon in combination with one or a plurality of atoms selected from the group consisting of O, S and N, including a mixture of such atoms; X=F, Cl, $CF_3$ and mixtures thereof; and m and n, independently, are an integer in the range of 1–3. These halogenated aromatic species have very low optical absorption losses when operating at telecommunications wavelengths. The linking groups W may be partially or fully halogenated and/or deuterated.

In another aspect, the invention is directed to a method of synthesizing highly halogenated aromatic compounds having polymerizable vinylic groups.

In yet another aspect, the invention is directed to energy polymerizable compositions that can used alone or in combination with other energy polymerizable compounds to form a polymeric material that has low optical losses in both the C-band and L-band. The energy polymerizable compositions contain (1) first polymerizable monomer of formula $P_2C=CH-C_6X_{4-n}Z_n$, where P=H or D, $Z=-Y-C_6X_5$, $-Y-W-U-[(o-, m-, p-C_6X_4-CH=CH_2)]_m$, and mixtures thereof; where, independently, Y and U=O, S, NH, or is not present; where W is a linking group selected from the group consisting of aromatic, polycyclic aromatic (fused-ring), 5- or 6-member heterocyclic aromatic and polycyclic-heterocyclic compounds and halogenated derivatives thereof; where X=F, Cl, $CF_3$ and $R_f$, and mixtures thereof, and $R_f$ is a $C_2$–$C_5$ hydrocarbon in which 50% or more of C—H bonds are replaced by C—F bonds; and where m and n are integers in the range of 1–3; (2) optionally, a second polymerizable monomer or oligomer having a polymerizable vinylic group; and (3) optionally, a polymerization initiator compound.

In yet another aspect, the invention is directed to optical elements and devices made from aromatic vinyl compounds having halogens and other selected substituents present on the aromatic ring

DETAILED DESCRIPTION OF THE INVENTION

As used herein the term "monomer 1 (or 2, 3, 4, or 5)" means a monomer of corresponding Structure 1, 2, 3, 4 or 5.

Also as used herein the term "polycyclic-heterocyclic "refers to a compound in which one or more nitrogen heterocyclic rings are "fused" to another heterocyclic ring or to one or more aromatic rings so that there are atoms common to the fused rings. The compound of Structure 4 exemplifies such a polycyclic heterocyclic ring linking two styryl moieties. The term "—N<(in ring)" as used herein means that the nitrogen atom is part of a heterocyclic ring as shown in FIG. 4.

The invention is directed to polymerizable vinyl-aromatic compounds in which the vinyl-bearing aromatic ring is halogenated and to a method of synthesizing such compounds. In particular, the invention is directed to polymerizable aromatic vinyl compounds wherein, except for the vinylic hydrogen atoms, aromatic C—H bonds are replaced by C—X bonds, where X is a halogen or other selected substituent and thus have a de minimus number, if any, of C—H bonds. In addition, the compounds of the invention have a de minimus number, if any, of N—H and O—H bonds. Such compounds are useful in manufacturing optical elements and devices for use in optical communications. The utility arises from that fact due to the absence or de minimus number of C—H, N—H and O—H bonds such compounds exhibit low optical absorbance losses at the wavelengths used in optical communications. In addition, the compounds of the invention contain aromatic rings, and in some instances sulfur atoms, which raise the refractive index of organic materials. High refractive index materials are also useful in the reparation of telecommunication elements and devices.

The compounds of the invention are energy polymerizable. Energy polymerizable means that they can be polymerized, either alone or in combination with other polymerizable compounds, by application of heat, actinic radiation or electron bean radiation to form homopolymers and/or copolymers. The energy polymerizable compositions contain (1) first polymerizable monomer of formula $P_2C=CH-C_6X_{4-n}Z_n$, where P=H or D, $Z=-Y-C_6X_5$, $-Y-W-U-[(o-, m-, p-C_6X_4-CH=CH_2)]_m$, and mixtures thereof; where, independently, Y and U=O, S, NH, or is not present; where W is a linking group selected from the group consisting of aromatic, polycyclic aromatic (fused-ring), 5- or 6-member heterocyclic aromatic and polycyclic-heterocyclic compounds and halogenated derivatives thereof; where X=F, Cl, $CF_3$ and $R_f$, and mixtures thereof, and $R_f$ is a $C_2$–$C_5$ hydrocarbon in which 50% or more of C—H bonds are replaced by C—F bonds; and where m and n are integers in the range of 1–3; (2) optionally, a second polymerizable monomer or oligomer having a polymerizable vinylic group; and (3) optionally, a polymerization initiator compound. The energy polymerizable composition may contain 1–99 wt. % of the first polymerizable monomer (or oligomer thereof); 1–99 wt. % of the optional second monomer (or oligomer thereof) and 0.001 10 wt. % of the optional initiator, and preferably from 0.1–6 wt. % of the initiator.

In one embodiment the invention is directed to the synthesis of compounds of general formula $P_2C=CH-C_6X_{4-n}Z_n$, where P=H or D, $Z=-Y-C_6X_5$, $-Y-W-U-[(o-, m-, \text{ or } p-C_6X_4-CH=CH_2)]_m$ and mixtures thereof; Y and U, independently =O, S, NH, or nothing; W is a linking group; n is an integer in the range of 1–3; and m is an integer in the range of 1–3.

The linking group W is selected from the group consisting of aromatic, polycyclic aromatic (fused-ring), 5- or 6-member heterocyclic aromatic and polycyclic-heterocyclic (fused ring) compounds in which at least one heterocyclic ring is fused to and aromatic ring, and halogenated derivatives of all the foregoing; X=F, Cl, CF$_3$ and mixtures thereof. The heterocyclic rings or the heterocyclic part of polycyclic-heterocyclic rings contain carbon in combination with one or a plurality of atoms selected from the group consisting of O, S and N, including a mixture of such atoms. The heterocyclic part of any W may also contain a —N<(in ring, originally as an imine or imide) part to which —CH=CH$_2$—C$_6$X$_4$ moiety can be attached. In addition, one or a plurality of the C—H bonds which may be present in W may be replaced by C—X bonds, where X=Cl, F, CF$_3$ or R$_f$, R$_f$ being a highly fluorinated C$_2$–C$_5$ hydrocarbon and highly fluorinated meaning that greater than 50% of C—H bonds are replaced by C—F bonds. Examples of W linking compounds include, without limitation, derivatives, including halogenated derivatives, of benzene and naphthalene having a general formula —C$_6$H$_{4-a}$X$_a$- or —C$_{10}$H$_{6-b}$X$_b$-, respectively, where a=1-4, b=1-6, and X=Cl, F, CF$_3$ or R$_f$, and the heterocyclic and polycyclic-heterocyclic compounds described herein.

Representative compounds of the type P$_2$C=CH—C$_6$X$_{5-n}$Z$_n$, where P=H or D, X=F and/or Cl, Z=—Y—C$_6$X$_5$, and Y=O, S or N, are those having the following Structures 1, 2 and 3.

A compound representative of the type P$_2$C=CH—C$_6$X$_{5-n}$Z$_n$, where P=H or D, X=F and/or Cl; Z=—Y—W—[U-o-, m-, or p-C$_6$X$_4$—CH=CH$_2$)]$_m$;where, independently, Y and U=O, S, NH or nothing; and where W is a selected aromatic or heterocyclic aromatic compound containing carbon in combination with one or a plurality of O, S and N is one having Structure 5: [2,5-bis[(2,3,5,6-tetrafluoro-4-vinylphenyl)thio]-1,3,4-thiadiazole. In this example Y and U are present and equal S.

An addition heterocyclic-containing compound representative of the invention is represented by Structure 6. The compound of Structure 6 contains a fluorinated styryl group N-bonded to a fluorinated maleimide moiety.

A polycyclic-heterocyclic (fused-ring) compound representative of the type P$_2$C=CH—C$_6$X$_{5-n}$Z$_n$, where P=H or D, X=F and/or Cl; Z=—Y—W—[U-o-, m-, or p-C$_6$X$_4$—CH=CH$_2$)]$_m$; n=1; and Y and U are not present is one having Structure 4. The compounds of Structure 4 is derived from 1,2,4,5-benzenetetracarboxylic acid diimide and contains two —N<(in ring) moieties as illustrated.

Heterocyclic aromatic compounds useful in practicing the invention are 5- and 6-member ring systems containing carbon in combination with at least one of sulfur, nitrogen and oxygen. In the heterocyclic ring systems there will be a degree of unsaturation due to the presence of double bonds (e.g., C=N, N=N, C=C). General examples of such 5- and 6-member heterocyclic ring systems are derivatives of the following which contain at least two thiol groups, an amino group and a thiol group, or a plurality of amino and/or thiol groups: pyridine, s- or as-thiazine, thiazoles, dithiazines, thiadiazines, pyrazine, pyrimidine, pyridazine, indolizine, imidazole, thiadiazoles, thiophene, furan and similar compounds known in the art. Further, in the foregoing derivatives C—X bonds may replace ring C—H bonds, where X is Cl, F or $CF_3$. Specific examples, without limitation, of such derivatives include 1,3,4-thiadiazole-2,5-dithiol; 5-amino-1,3,4-thiadiazole-2-thiol; trithiocyanuric acid; 4-amino-2-mercaptopyrimidine; 2,4-diamino-6-mercaptopyrimidine; 4,6-diamino-2-mercaptopyrimidine; 4,5-diamino-2,6-dimercaptopyrimidine, and similar compounds known in the art. When dithiol compounds are used, the final vinylic compounds in accordance with the invention will have a structure similar to that of Structure 5. When a compound having at least one thiol group and one amino group is used, the final product will be expected to have one styryl moiety, $(P_2C=CH)—C_6X_4—$, where P=H or D, X is Cl. F or $CF_3$, replacing only one amino hydrogen atom due to steric considerations. The scope of the invention includes any of the above compound and similar compounds in which heterocyclic ring C—H bonds have been replaced by C—X bonds, where X=F, Cl, $CF_3$, $R_f$ ($R_f$ being defined elsewhere in this application) and D (deuterium).

Polycyclic heterocyclic compounds useful in practicing the invention are those in which at least one heterocyclic ring is fused to an aromatic ring. Examples of such compounds include, without limitation, 1,2-difluoro-2,3,5,6-benzenetetracarboxylic acid diimide, alloxazine {benzo[g]pteridine-2,4(1H,3H)-dione}, 2-amino-6-chloropurine, 2-amino-6-hydroxy-8-mercaptpurine, 5-aminoindazole, 5-aminoindole, 1-aminopyrine, 2-amino-6-purinethiol and similar compounds known in the art, and halogenated derivatives thereof.

The compounds of the invention can be used in the preparation of polymers and copolymers slated for use in optical communications applications. In some applications where high refractive indices are desired, compounds of the invention containing sulfur atoms will be found to be particularly advantageous. Sulfur atoms are also particularly advantageous when the polymer is in contact with metal electrodes or substrates because they improve adhesion. The halogenated aromatic vinyl compounds of the invention, also known as halogenated styrene compounds, can be homopolymerized or copolymerized with other polymerizable compounds having polymerizable carbon-carbon double and triple bonds. Examples of other compounds suitable for copolymerization by methods known in the art include other vinylic compounds including other styrene compounds, vinyl sulfides, acrylates, methacrylates, olefins, acetylene compounds, thiols and polythiols (to form thiolene compounds) and similar compounds, including halogenated derivatives of any of the foregoing. Particularly advantageous is the use of compounds of the invention with acrylates and methacrylates, and especially fluorinated acrylates and methacrylates of general formula $CH_2=CA—C(O)—R_{f2}$, where A=H, $CH_3$, $CF_3$ and $R_{f2}$, and $R_{f2}$ is a highly fluorinated $C_1–C_{10}$ alkyl group. Mixtures of the foregoing compounds can also be used in forming copolymers with the compounds of the invention. For example, the compound of Structure 1 can be copolymerized with a mixture of fluorinated acrylates and/or methacrylates. Copolymers can be made using 1–99% of the monomer of the invention with 1–99% of a second monomer as specified herein. The monomers of the invention can also be oligomerized and these oligomers can be polymerized with second monomers as specified herein or oligomers of such second monomers.

When homopolymerized the monomer of the invention may optionally include an appropriate thermal initiator or photoinitiator such as one of those described below. Also optionally, the monomers of the invention can be mixed with a selected second monomer or oligomer and, optionally, a selected thermal initiator or photoinitiator. Further, if the resulting composition is too viscous to be used for the desired application, an selected solvent (for example, THF, acetone, methyl ethyl ketone) can be added in an amount sufficient to make a solution appropriate viscosity.

When preparing optical devices or elements, the composition can be applied to a substrate by any method known in the art; for example, by spraying, dipping, spin coating, or painting the composition on the substrate. A photomask may then be applied if required and the composition cured as described herein. Uncured composition can be removed by the use of an appropriate solvent. Subsequently, such additional processing steps as may be required to make the element or device can be undertaken.

The compounds of the invention can be homopolymerized or copolymerized as described above. Such polymerization is facilitated by the use of actinic radiation, usually UV or visible light, or electron beam radiation, preferably in the presence of a photoinitiator compound. Any photoinitiator known in the art to be useful for the polymerization of carbon-carbon multiple bonds can be used for such polymerizations. Such initiators may be used on amounts of 0.01–10 wt. %, preferable from 0.1 to 6 wt. % of the total polymerizable mixture. Examples of such photoinitiators, without limit, include aromatic ketones such as benzophenone, acrylated benzophenone, 2-ethylanthraquinone, phenanthraquinone, benzyl dimethyl ketal and other aromatic ketones, for example, benzoin, benzoin ethers such as benzoin methyl ether, benzoin isobutyl ether, benzoin phenyl ether, methyl benzoin and other benzoin compounds. Typical commercially available photoinitiators include 1-hydroxycyclohexyl phenyl ketone (Irgacure® 184), benzoin, benzoin ethyl ether, benzodimethyl ketal (Irgacure 651, Ciba-Geigy), 2,2-diethylacetophenone, 2-hydroxy-2-methyl-1-phenylpropan-1-one (Darocur® 1173, Ciba-Geigy), 1-[4-(2-hydroxyethoxy)phenyl]-2-morpholinopropan-1-one (Darocur 2959), 2-methyl-1-[4-(methylthio)phenyl]-2-morpholinopropan-1-one (Irgacure 907), 2-benzyl-2-dimethylamino-1-(4-morpholinophenyl)butan-1-one (Irgacure 369), poly{1-[4-(1-methylvinyl)phenyl]-2- hydroxy-2-methylpropan-1-one} (Esacure® KIP, Lamberti S.p.A., Gallarate, Italy) and [4-(4-methylphenylthio)-phenyl]phenylmethanone (Quantacure® BMS, Great Lakes Fine Chemicals Ltd., London, Great Britain). The most desired photoinitiators are those that do not tend to yellow upon irradiation. Darocur 1173, Irgacure 651, Irgacure 184 and Darocur 2959 mentioned above are specific examples. For highly halogenated curable compositions including the compounds of the invention, particularly where the halogen is fluorine, photoinitiators such as L-12043 and L-9367 from 3M or a fluorinated photoinitiator such as 2-(1H, 1H,2H, 2H-heptadecafluoro-1-decoxy)-2-methyl-1-phenylpropan-1-one (described in U.S. Pat. No. 5,391,587) may be required.

Thermal initiators, which generate free radicals upon heating, may also be used in selected amounts to initiate the polymerization of polymerizable (curable) compositions containing the compounds of the invention. Examples of such thermal initiators, without limitation, include substituted or unsubstituted organic peroxides, azo compounds, pinocols, thiurams, and mixtures thereof. Specific examples, without limitation, include benzoyl peroxide, p-chlorobenzoyl peroxide, cumene hydroperoxide, 1,2-di(tert-butylperoxy)-3,3,5-trimethylcyclohexane, 2,2'-azo-bis-isobutyrylnitrile (AIBN), (1-phenylethyl)azodiphenylmethane, dimethyl-2,2'-azobis(1-cyclohexanecarbonitrile) and 2,2'-azobis(2-methylpropane).

The free radical generating initiator, either photo or thermal, may be present in the polymerizable compositions in a selected amount sufficient to effect polymerization of the composition upon exposure to sufficient energy of the appropriate type. For example, a photoinitiator is present in an amount sufficient to effect polymerization upon exposure to actinic radiation; generally in an amount in the range of approximately 0.01 to 10 wt. % of the overall composition, but more usually in the range of approximately 0.1–6 wt. %. Mixtures of different initiators can be use. In certain instances, for example, when curing by use of electron beam radiation, the composition may not require a free radical initiator since such free radicals may be generated in situ by the electron beam. In such instances the use of the initiator may be considered optional, and it may be included to facilitate or speed-up polymerization. Additional examples of photo- and thermal initiators may be found in publications known to those skilled in the art; for example, W. R. Sorenson and T. W. Campbell, *Preparative Methods in Polymer Chemistry*, 2$^{nd}$ Ed. (Interscience Publishers, New York 1968).

The following non-limiting examples serve to illustrate the compounds of the invention and the method of making such compounds.

Synthesis of the Compound of Structure 1.

The compound of Structure 1,3,5-difluorotris-2,4,6-(pentafluorophenyloxy)-styrene, was prepared according to the following overall reaction scheme, which is further described in Examples 1 and 2.

EXAMPLE 1

Preparation of tris(pentafluorophenyloxy)benzaldehyde

Formula: $C_{25}HF_{17}O$ Molecular Weight: 688.25 g/mol.

Reaction

Pentafluorobenzaldehyde (30.00 g; 0.152 mol; 196.02 g/mol; 1 eq.), potassium carbonate (34.89 g; 0.253 mol; 138.2 g/mol; 1.65 eq., 18-crown-6 ether (18-C-6, 13.35 g; 0.051 mol; 264.32 g/mol; 0.33 eq.), and dry THF (60 ml; 2v) were introduced in a reactor. The mixture was stirred and refluxed gently (bp=67° C.). A solution of pentafluorophenol (92.96 g; 0.505 mol; 184.08 g/mol; 3.3 eq.) and dry THF (60 ml) was dropped slowly into the reactor over about 1 hour. The reaction mixture became yellow. The mixture was refluxed during 3 days and the end is controlled by TLC (silica; toluene/heptane 50/50; $R_f$=0.66). If the mixture is too compact (e.g., by formation of KF and/or evaporation of THF through the joint), dry THF was added to compensate.

When the reaction was completed, 400 ml of water were added and the mixture was filtrated. The pink solid was washed by water and then dried in a dessicator. The yield of dry pinkish crude solid m=91.6 g (87%)

Purification:

The pink solid (m=91.6 g) was recrystallized from isopropyl alcohol, THF and water. The solid was dissolved by refluxing isopropyl alcohol (450 ml) followed by the slow addition of THF (approximately 50 ml) until the solution becomes clear. Water (200 ml) was added and a white solid precipitated from the refluxing mixture. This solution was cooled at 5° C. in ice/water slush, filtrated and the solid was washed with 60 ml of cold isopropyl alcohol. A purified white solid was obtained, m=49.63 g (54% from the crude mixture; 47% from pentafluorobenzaldehyde).

Analysis:

Mp=132° C.

TLC: (silica $C_{18}$; methyl alcohol and water 90/10) $R_f$=0.26

IR ($cm^{-1}$): 1709.00 (C=O aldehyde), 1624.36; 1517.9 (C—F); 1490.85; 1473.40; 1392.84; 1366.94; 1311.09; 1288.4; 1166.97; 1099.12; 1034.72; 989.72; 948.17; 905.94; 822.62; 731.07; 621.45; 602.18

EXAMPLE 2

Preparation of 3,5-difluorotris-2,4,6-(pentafluorophenyloxy)styrene

Formula: $C_{26}H_3F_{17}O_3$ Molecular Weight: 686.28 g/mol

Reaction

Triphenylphosphonium methylide was prepared under nitrogen from sodium hydride and methyl triphenylphosphonium bromide in anhydrous THF. Sodium hydride (1.16 g, 0.029 mol; 24 g/mol; 2.0 eq., 60% mineral oil dispersion) was washed with anhydrous pentane (3×10 ml). The residual pentane was removed under vacuum. Under nitrogen, methyl triphenylphosphonium bromide (6.22 g; 0.0174 mol; 357.24 g/mol; 1.2 eq.) and dry THF (100 ml) were mixed together and the mixture (white) was stirred at room temperature for approximately 15 minutes. Trisfluorophenolbenzaldehyde (10.0 g; 0.0145 mol; 688.25 g/mol; 1 eq.) was slowly added in small portions over approximately 20 minutes to the white mixture. The resulting was yellow. The reaction was stirred at room temperature and the end point determined by TLC (silica; toluene/heptane 20/80; $R_f$=0.80). At completion the reaction mixture was brown.

When there is no more starting product, toluene (100 ml) was added and the resulting mixture was slowly quenched with water (100 ml). The aqueous layer was extracted with 50 ml of toluene. Organic layers were combined and washed with water (60 ml); aqueous ammonium chloride at 10% (2×80 ml); and saturated aqueous sodium chloride (100 ml). The organic layer was then dried with potassium sulfate, filtrated, stabilized with 500 ppm 4-tert-buthylcathecol (TBC) and evaporated. The residue is a brown oil (m=7.26 g; 73%) which contains small amounts of triphenylphosphine oxide.

This oil was dissolved in a minimum amount of toluene and filtrated on silica. The resulting filtered solution was stabilized with 500 ppm TBC before being concentrated to an orange solid, m=6.27 g (63%).

Purification

The orange solid was dissolved in refluxing ethanol and 10% (0.6 g) of active carbon was added. The mixture was stirred for approximately 5 minutes then hot filtrated on cellite. The filtrate was left standing to recrystallize. The purified solid is white.

Analysis

TLC: (silica; toluene and heptane 20/80) $R_f$=0.80

TLC: (silica C18; ethyl alcohol) $R_f$=0.65

Synthesis of the Compound of Structure 5.

EXAMPLE 3

Preparation of Dialdehyde

Formula: ($C_{18}H_2F_8N_2O_3S_2$) Molecular Weight: 502.37 g/mol

The divinyl compound of Structure 5 was prepared according to the following reaction scheme:

Reaction: Preparation of the Dialdehyde Intermediate $C_{16}F_8N_2O_2S_2$

The dialdehyde intermediate shown in the scheme above, 4,4'-[1,3,4-thiadiazole-2,5-diylbis(thio)]bis[2,3,5,6-tetrafluoro]benzaldehyde, was prepared in a manner in accordance with Example 1, except that 2,5-dimercapto-1,3,4-thiadiazole was used in place of pentafluorophenol. The resulting dialdehyde, 2,5-bis(4-aldehydo-2,3,5, 6-tetrafluorophenymercapto)-1,3,4-thiadiazole, was isolated and used to prepare the divinyl compound of Structure 5.

Pentafluorobenzaldehyde (20.0 g; 0.120 mol; 196.02 g/mol; 1 eq.), potassium carbonate (15.5 g; 0.112 mol; 138.2 g/mol; 2.2 eq.), 18-crown-6 ether (1.35 g; $5.1 \times 10^{-3}$ mol; 264.32 g/mol; 0.1 eq.) and anhydrous THF (80 ml) were introduced into a reactor and stirred. The resulting solution was yellow.

A solution of 2,5-dimercapto-1,3,4-thiadiazole (7.66 g; 0.0515 mol; 150.23 g/mol; 0.5 eq.) in anhydrous THF (30 ml) was then added at room temperature to the reactor over approximately 1 hour. The reaction end point was controlled by TLC (silica; toluene, $R_f$=0.3). The mixture was composed of two phases: a yellow solid and a brown liquid.

When there was no more pentafluorobenzaldehyde, the mixture was quenched with 200 ml of water and extracted with 100 ml of dichloromethane. The aqueous layer was then extracted with dichloromethane (3×100 ml). The combined organic extracts were washed with water until neutral pH. The organic layer was then washed with 100 ml of saturated aqueous sodium chloride, dried with potassium sulfate, filtered, and concentrated. Subsequently, the organic solution was concentrated (before crystallization) and this solution was filtrated on silica. The filtered solution was concentrated and yielded 21.7 g (84%) of a slightly yellow oil which crystallized to white solid on standing.

Analysis

Mp=132° C.

TLC: (silica $C_{18}$, methanol/water 9/1) $R_f$=0.74

IR (in cm$^{-1}$): 1710.6 (C=O aldehyde); 1640.69; 1474.05 (C—F); 1419.35; 1380.17; 1349.52; 1285.64; 1037.22; 996.89; 968.24; 849.46; 787.80; 631.04

EXAMPLE 4

Preparation of The Divinyl Compound of Structure 5

2,5-bis[(4-ethenyl-2,3,5,6 tetrafluorophenylsulfanyl]-1,3,4-thiadiazole

Formula: $C_{18}H_6F_8N_2S_3$ Molecular Weight:; 498.42 g/mol

Reaction.

Triphenylphosphonium methylide was prepared under nitrogen from sodium hydride and methyltriphenylphosphonium bromide in anhydrous THF. Sodium hydride (2.86 g, $7.17 \times 10^{-2}$ mol; 24 g/mol; 2.4 eq., 60% mineral oil dispersion) was washed with anhydrous pentane (3×50 ml). The residual pentane was removed under vacuum. Under nitrogen, dry THF (200 ml) and methyltriphenylphosphonium bromide (25.6 g; $7.17 \times 10^{-2}$ mol; 357.24 g/mol; 2.4 eq.) were mixed. The resulting white mixture was stirred at room temperature for approximately 15 minutes. Subsequently, the dialdehyde (15.0 g; $2.98 \times 10^{-2}$ mol; 502.37 g/mol; 1 eq.) from Example 3 was added slowly to the white mixture in small portions over approximately 30 minutes. The color of the resulting mixture was brown (milk-coffee color). The reaction was then stirred at room temperature and the end point determined by TLC (silica; toluene; $R_f$=0.65). When there is no more dialdehyde or intermediate compound, toluene (100 ml) was added and the mixture was then slowly quenched with water (200 ml). The aqueous layer was extracted with 100 ml of toluene. Organic layers were combined and washed with water (200 ml); aqueous chloride ammonium at 10% (200 ml); and saturated aqueous sodium chloride (200 ml). The organic layer was then dried with potassium sulfate, filtrated, stabilized with 1000 ppm of 4-tert-butylcatechol (TBC) and evaporated. The residue was a brown oil (14.78 g) that contained triphenylphosphine oxide.

This brown oil was dissolved in a minimum of toluene and filtrated on silica. The resulting solution was then stabilized with 1000 ppm TBC before concentrating to obtain a yellow solid m=11.13 g (75%) which contained a small amount of an unknown impurity.

Purification

The yellow solid (m=11.13 g) was recrystallized from ethanol and water. The solid was dissolved in refluxing ethanol. When the solution was limpid, water was added until the solution becomes cloudy (approximately 23% of water). This solution was cooled very slowly at room temperature. The resulting white solid was filtrated and washed with cold ethanol. White solid m=7.79 g (81%)

Analysis

TLC: (silica; toluene) $R_f$=0.65

IR (cm$^{-1}$): 3092.60 and 3032.15 (R—CH=CH2); 1600.01; 1488.16 (C—F), 1437.90; 1384.41; 1266.06; 1235.26; 1194.73; 1178.52; 1129.89; 1118.54; 1053.70; 914.28 and 893.21 (deformation of CH=CH2); 864.03; 711.64; 669.49; 645.17

EXAMPLE 5

Synthesis of the Compound of Structure 2.

The compound of Structure 2, 3,5-difluorotris-2,4,6-(pentafluorothiophenyloxy)styrene, was prepared according to the procedures used in Examples 1 and 2 to prepare 3,5-difluorotris-2,4,6-(pentafluorophenoxy)styrene, except that pentafluorothiophenol was used in place of pentafluorophenol.

EXAMPLE 6

Synthesis of the Compound of Structure 3.

The compound of Structure 3, 3,5-difluorotris-2,4,6-(pentachlorophenyloxy)styrene, was prepared according to the procedures used in Examples 1 and 2 to prepare 3,5-difluorotris-2,4,6-(pentafluorophenoxy)styrene, except that pentachlorophenol was used in place of pentafluorophenol.

EXAMPLE 7

Synthesis of Mixed Compounds

Compounds having a mixture of pentafluorophenoxy and pentafluorothiophenoxy groups can be prepared using methods described herein. Since such reactions may result in a mixture of compounds, separation techniques such as column chromatography, fractional crystallization, thin plate chromatography and similar methods known in the art may be required to separate different compounds. To prepare such compounds one would adjust the phenolic content so that the total phenol comprises, for example, 1-part pentafluorophenol and two parts pentafluorothiophenol, or visa versa. Adjusting the phenolic component in such a manner will result in a compound containing one pentafluorophenoxy groups and two pentafluorothiophenoxy groups, or visa versa, or a mixture of compounds which may be separated. Other combinations of pentafluorophenol, pentachlorophenol and pentafluorothiophenol are possible and are deemed to be within the scope of the invention.

EXAMPLE 8

Other Heterocycle-Containing Styrene Compounds

Trithiocyanuric acid (1,3,5-triazine-2,4,6-trithiol), $C_3N_3(SH)_3$, a C—N heterocyclic compound having three pendent —SH groups, can be used in place of 2,5-dimercapto-1,3,4-thiadiazole in reactions according to Examples 3 and 4 to form a product, 2,4,6-tris(4-ethenyl-2,3,5,6-tetrafluorophenyl)-1,3,5-triazine, having three pendent tetrafluorostyryl groups wherein the vinyl is the para position relative to the sulfur atom. Other heterocyclic compounds having two or more pendent —SH groups can be used to prepare similar compound in accordance with the invention.

EXAMPLE 9

Polymerizable Compositions

A polymerizable composition is prepared comprising 40 parts by weight the compound of Structure 1, 58 parts by weight of an acrylate of formula $CH_2$=CA—C(O)—O—$R_{f2}$, where A is $CF_3$ and $R_{f2}$ is a highly fluorinated $C_2$ alkyl group, and 2 parts by weight Darocur 1173 as a photoinitiator. The composition is spin coated on a silicon substrate having an undercladding layer previously applied thereto and is then UV cured through a photomask to form a waveguide structure. Uncured composition is removed by use of a solvent and an overcladding layer is applied.

Figure 1:
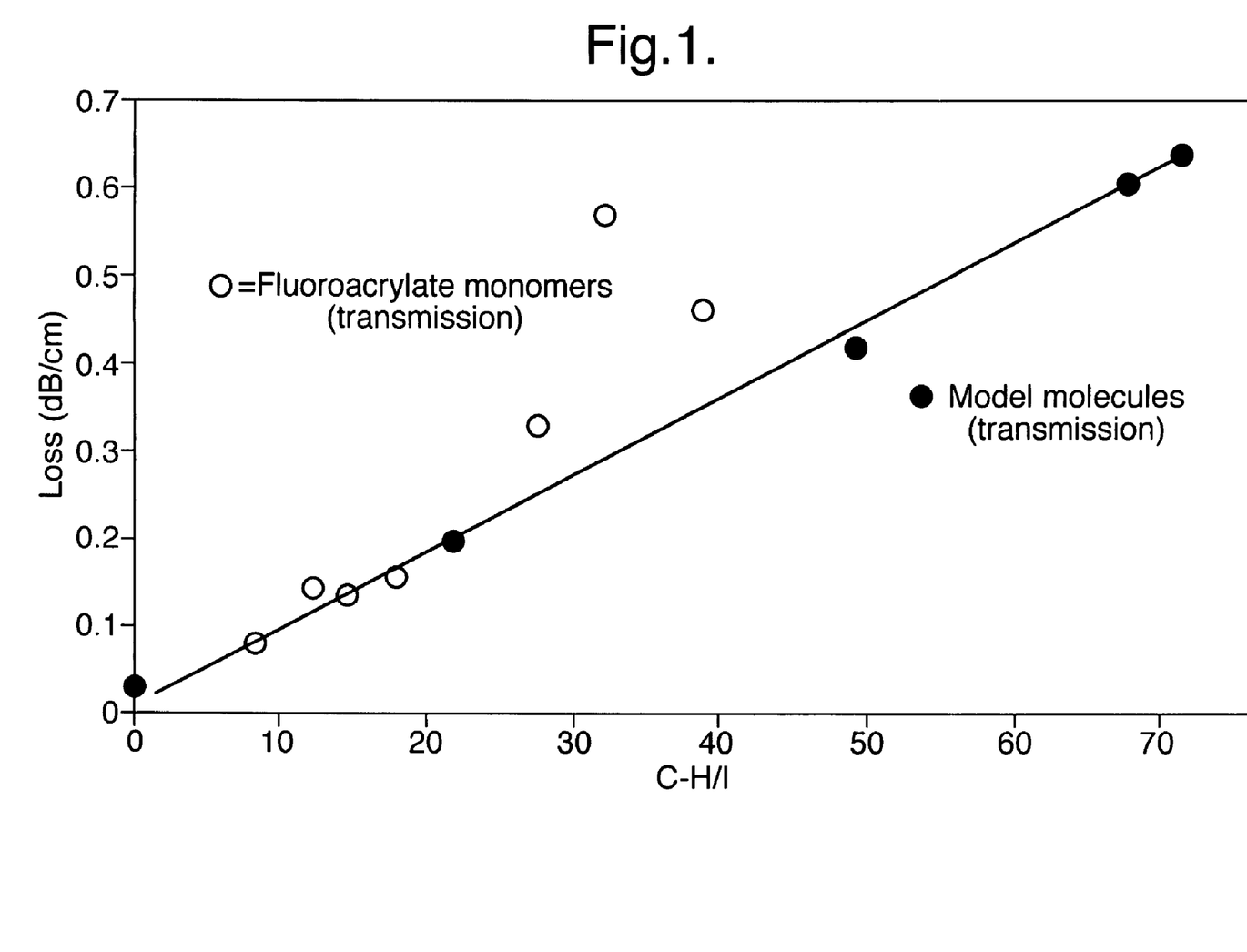
FIG. 1 illustrates the absorption or propagation losses for various molecules versus H per unit volume.

Compounds containing a combination of —SH and —$NH_2$ groups can also be used to prepare styryl derivatives in accordance with the invention. For example, 5-amino-1,3,4-thiadiazole-2-thiol can be used in reactions according to Examples 3 and 4 to prepare a compound having the invention formula (p-$H_2C$=CH—)$C_6F_4$—NH—$C_2N_2S$—$C_6F_4$-(p-CH=$CH_2$). In another example, 4,5-diamino-2,6-dimercapto-pyrimidine can be used in reactions according to Examples 3 and 4 to prepare compound in which the sulfur and/or the amino groups have pendent tetrafluorophenyl-styryl groups. An addition example of an amino bearing compound that can be used in practicing the invention is:

Absorption losses at 1550 nm are linked to C—H overtones and combinations bands. The absorption losses at 1550 nm of several organic molecules having various amounts of C—H bonds per volume unit and no C—H or C-h bonds were measure using 1 mm and 10 mm optical paths to cancel error due to interfacial reflection or diffusion. FIG. 1 illustrates the results obtained for model molecules (hexafluorobenzene, pentafluorostyrene, phenyl trimethylsilyl acetylene and epithiopropyl methacrylate, shown as "●" in FIG. 1) and for fluoroacrylate monomers known in the art which bear fluoroalkoxy and fluoroalkyl chains (shown as "o" in FIG. 1) such as monomers described in U.S. Pat. Nos. 6,303,563, 6,335,149 and 6,323,361 (for example, compounds of general formula A-$R_1$-$R_f$-$R_2$-A and A-$R_1$-$R_f$-$R_3$, where A is a polymerizable group such as $Y_2C$=C(X)COO—; $R_1$ and $R_2$ are alkyl, aromatic, ester, ether, $CF_2$ and similar connecting groups; $R_3$ is $CF_3$, $CH_3$, H or D; X is H, D, F, Cl, $CF_3$ or $CH_3$; Y is H or D; and $R_f$ is a fluorinated connecting group such as —$(CF)_x$-, where x is 1–10. Exemplary monomers are $H_2C$=C(F)—C(O)O—$CH_2(CF_2)_2CH_2$—O(O)C—C(F)=$CH_2$, $H_2C$=C(F)—C(O)O—$CH_2(CF_2)_2CH_3$ and $H_2C$=C(F)—C(O)O—$CH_{2(CF2)2}CF_3$. The amount of C—H per volume unit ("H/vol (I)" in FIG. 1) was estimated for the monomers. For monomers Structures 1, 2, and 3, the number of H/I is below 10, resulting in an absorption loss estimate below 0.1 dB/cm. The estimated H/I ratio for the monomer of Structure 1 (Compound 1) is approximately 7, resulting in a loss of 0.088 dB/cm using the linear regression curve developed from the model molecules.

Free-radical homopolymerization of the monomer of Structure 1, a cream-white solid, was done in THF solution (800 mg of compound 1 in 20 ml THF, under nitrogen, 16 hours refluxed), with azo-bis-isobutyrylnitrile (AIBN, 2 wt. %) as the initiator. A pale colored polymer was obtained. The reaction was followed by FT-IR spectroscopy.

Figure 2:
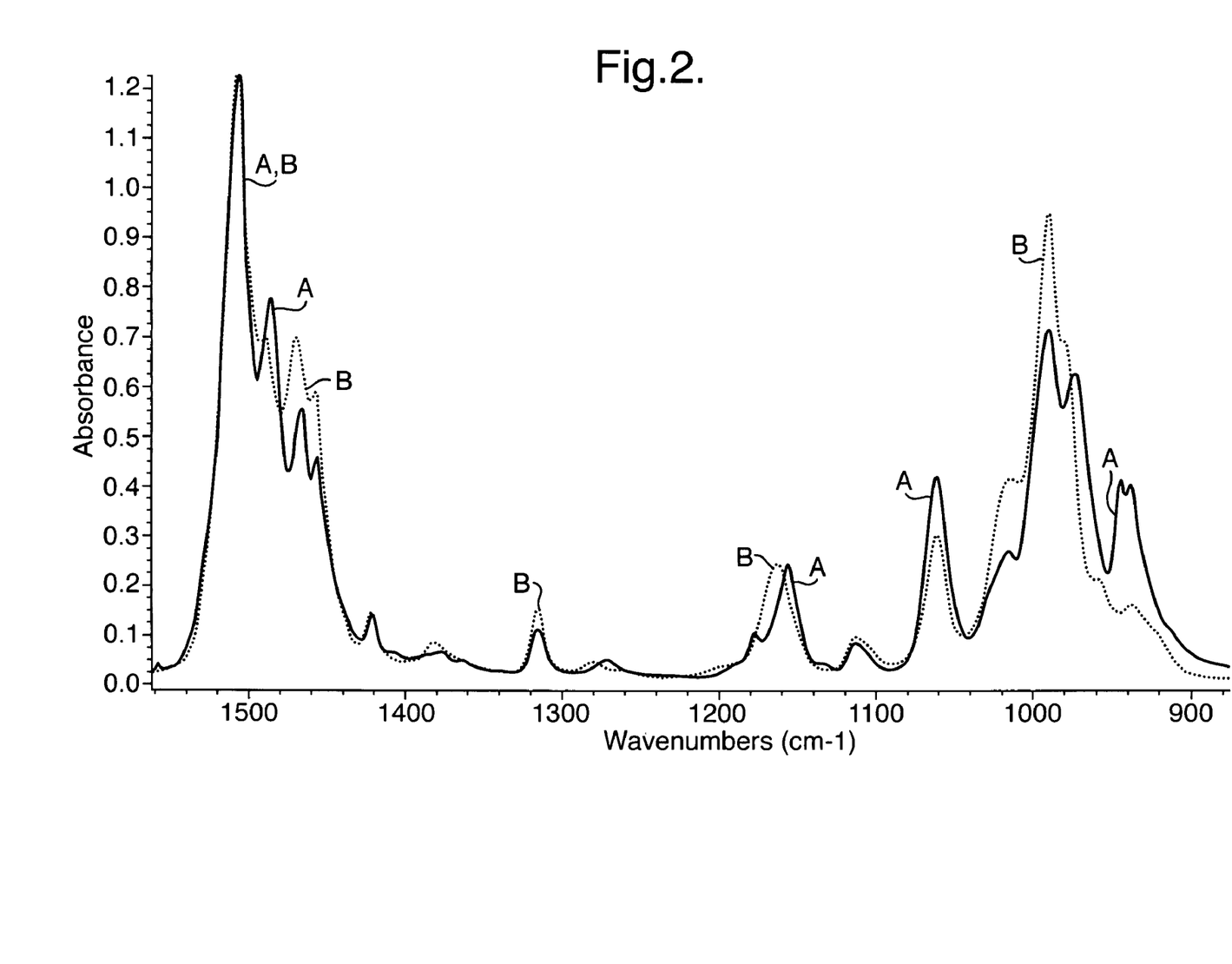
FIG. 2 illustrates the FT-IR spectrum for a monomer of Structure 1 and a homopolymer formed from the polymer.

FIG. 2 shows the FT-IR spectrum of monomer 1 (A, blue) superimposed on the spectrum of the polymer (B, red). In the monomer spectrum bands appears between 900 and 1000 $cm^{-1}$. These bands can be attributed to deformation vibration of RHC=$CH_2$ vinyl bonds. These bands have almost disappeared in the polymer spectrum, indicating that the vinyl bonds have disappeared as expected for a polymerized product.

Figure 3:
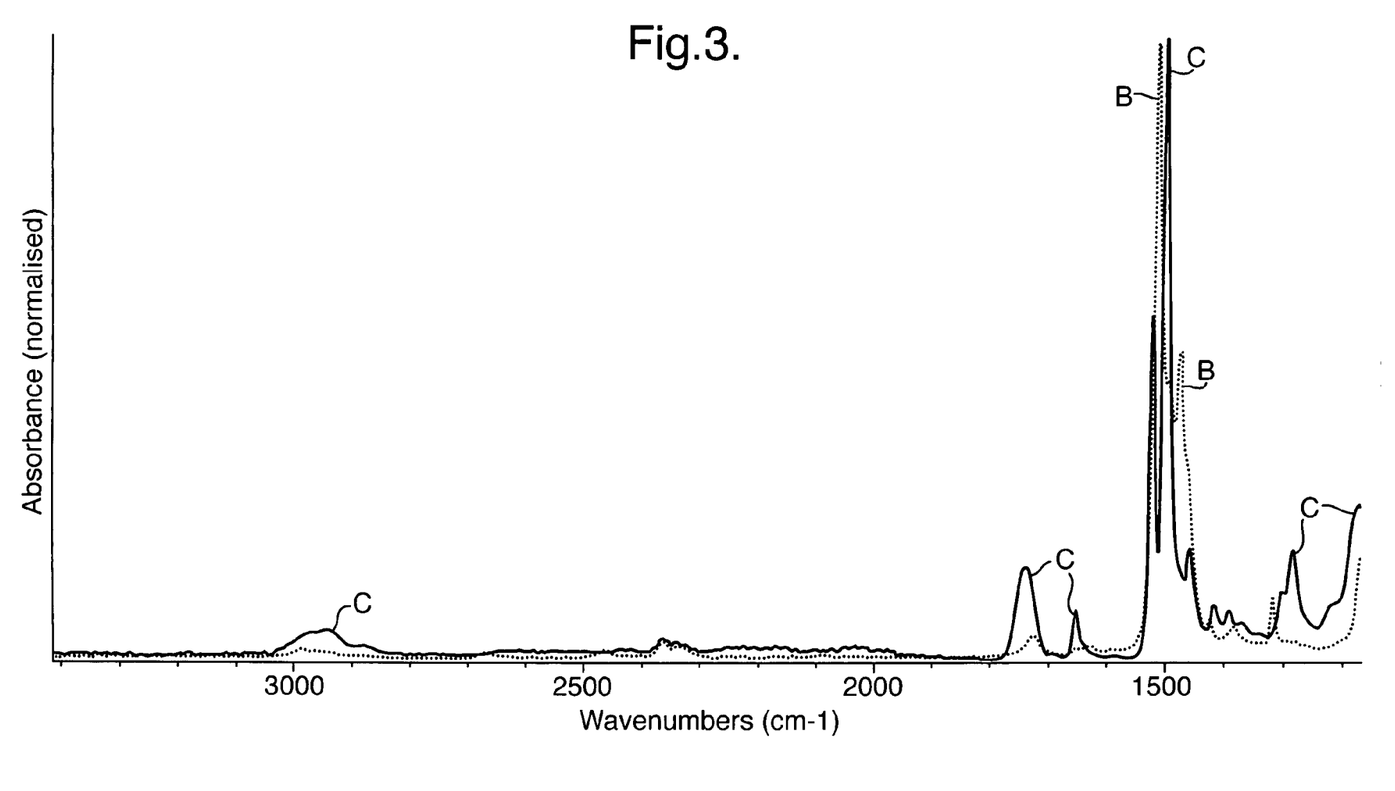
FIG. 3 illustrates the FT-IR of a homopolymer made from the monomer of Structure 1 and a copolymer made from monomer 1 and a fluorinated epoxy monomer.

FIG. 3 shows the FT-IR spectrum of polymerized compound 1 (B, red) and the FT-IR spectrum of copolymer 12 (C), a vinyl-epoxy fluoropolymer used as core material for waveguides. Spectra are normalized to highest peak corresponding to the C=C bands. The bands appearing between 2800 and 3100 $cm^{-1}$ are attributed to the C—H stretching vibration. The bands are much weaker for B than for C. Consequently, when B is used in telecommunications applications a much smaller contribution to absorbance losses due to C—H overtone and combination bands at 1550 nm is to be expected. The epoxy monomer used to prepare the copolymer was composed of 10 wt. % of gycidylmethacrylate, 15 wt. % of trifluoroethylmethacrylate and 75 wt. % of pentafluorostyrene.

It will be apparent to those skilled in the art that various modifications and variations can be made to the present invention without departing from the spirit and scope of the invention. Thus it is intended that the present invention cover the modifications and variations of this invention provided that they come within the scope of the appended claims and their equivalents.

What is claimed is:
1. An energy polymerizable composition comprising:
    (a) a first polymerizable monomer of formula $P_2C$=CH—$C_6X_{4-n}Z_n$, where
    (I) P=H or D, Z=—Y—$C_6X_5$, —Y—W—U-[(o-, m-, p-$C_6X_4$—CH=$CH_2$)]$_m$, and mixtures thereof;
    (ii) independently, Y and U=O, S, NH, or is not present;
    (iii) W is a linking group selected from the group consisting of aromatic, polycyclic aromatic (fused-ring), 5- or 6-member heterocyclic aromatic and polycyclic-heterocyclic compounds and halogenated derivatives thereof;
    (iv) X=F, Cl, $CF_3$ and $R_f$, and mixtures thereof, and $R_f$ is a $C_2$–$C_5$ hydrocarbon in which 50% or more of C—H bonds are replaced by C—F bonds; and
    (v) M and n are integers in the range of 1–3;
    (b) optionally, a second polymerizable monomer or oligomer having a polymerizable vinylic group; and
    (c) optionally, a polymerization initiator compound.
2. The composition according to claim 1, wherein in said first monomer W is a 5- or 6-member heterocyclic ring systems having pendent from the heterocyclic ring at least two thiol groups, or an amino group and a thiol group, or a plurality of amino and/or thiol groups.

3. The composition according to claim 2, wherein in said first monomer the heterocyclic ring is selected from the group consisting of pyridine, s- or as-thiazine, thiazoles, triazines, dithiazines, thiadiazines, pyrazine, pyrimidine, pyridazine, indolizine, imidazole, thiadiazoles, thiophene, furan, and halogenated derivatives thereof, and similar compounds known in the art.

4. The composition according to claim 3, wherein in said first monomer the heterocyclic aromatic ring is selected from the group consisting of 1,3,4-thiadiazole-2,5-dithiol; 5-amino-1,3,4-thiadiazole-2-thiol; trithiocyanuric acid; 4-amino-2-mercaptopyrimidine; 2,4-diamino-6-mercaptopyrimidine; 4,6-diamino-2-mercaptopyrimidone; 4,5-diamino-2,6-dimercaptopyrimidine, and halogenated derivatives thereof, and similar compounds known in the art.

5. The composition according to claim 1, wherein one or both of U and Y is not present, and W is a polycyclic heterocyclic ring, including halogenated derivatives thereof, having an —N<(in ring) moiety in place of said absent Y or U.

6. The compounds according to claim 5 wherein W is selected from the group consisting of 1,2-difluoro-2,3,5,6-benzenetetracarboxylic acid diimide, alloxazine {benzo[g]pteridine-2,4(1H,3H)-dione}, 2-amino-6-chloropurine, 2-amino-6-hydroxy-8-mercaptorine, 5-aminoindazole, 5-aminoindole, 1-aminopyrine, 2-amino-6-purinethiol and similar compounds known in the art, and halogenated derivatives thereof.

7. The composition according to claim 1, wherein in said first monomer Z is selected from the group consisting of —O—C$_6$F$_5$, —O—C$_6$Cl$_5$, —S—C$_6$F$_5$, —S—C$_6$Cl$_5$, and mixtures thereof, and n=3.

8. The composition according to claim 1, wherein in said first monomer n=1 and Z is:

-continued
or or

9. The composition according to claim 1, wherein said second monomer is selected from the group consisting of styrene compounds, vinyl sulfides, acrylates, methacrylates, olefins, acetylene compounds, thiols and polythiols and similar compound having carbon-carbon multiple bonds, and mixtures of the foregoing, and halogenated derivatives of any of the foregoing.

10. The composition according to claim 9, wherein said second monomer is an acrylate, a methacrylate, or mixtures of one or more thereof, including halogenated derivatives thereof.

11. The composition according to claim 9, wherein said second monomer is a fluorinated acrylate or methacrylate of general formula CH$_2$=CA—C(O)—O—R$_f$, or a mixture of one or more thereof, where A=H, CH$_3$, CF$_3$ and R$_{f2}$, and R$_{f2}$ is a highly fluorinated C$_{1-C10}$ alkyl group.

12. The composition according to claim 1, wherein said composition includes said optional initiator, and said initiator is a thermal initiator or free radical initiator.

* * * * *